United States Patent [19]

Sato et al.

[11] 4,377,718

[45] Mar. 22, 1983

[54] PROCESS FOR PRODUCING P-XYLENE

[75] Inventors: Kimihiko Sato; Tokuji Sakai; Yasuo Yamasaki; Tamio Onodera; Koji Sumitani, all of Matsuyama, Japan

[73] Assignee: Teijin Petrochemical Industries Ltd., Tokyo, Japan

[21] Appl. No.: 285,464

[22] Filed: Jul. 21, 1981

[30] Foreign Application Priority Data

Jul. 25, 1980 [JP] Japan ................................. 55-101220

[51] Int. Cl.$^3$ .............................................. C07C 2/68
[52] U.S. Cl. .................................................. 585/467
[58] Field of Search ........................................ 585/467

[56] References Cited

U.S. PATENT DOCUMENTS

| 4,250,345 | 2/1981 | Chu ..................................... 585/467 |
| 4,278,565 | 7/1981 | Chen et al. ...................... 252/455 Z |
| 4,302,622 | 11/1981 | Chu ..................................... 585/467 |

*Primary Examiner*—Curtis R. Davis
*Attorney, Agent, or Firm*—Sherman & Shalloway

[57] ABSTRACT

In a process for producing p-xylene which comprises catalytically methylating toluene with a methylating agent in the gaseous phase, the improvement wherein (a) said methylation is carried out continuously in a multi-stage reaction system consisting of a plurality of separate series-connected fixed catalyst layers without separating the resulting xylenes in an intermediate stage, (b) said toluene is fed together with hydrogen gas into only the first-stage fixed catalyst layer and passed successively through the subsequent fixed catalyst layers, the amount of toluene fed being such that the total weight hourly space velocity of toluene is from 1 to 300 hr$^{-1}$, (c) said methylating agent is fed into each of said fixed catalyst layers, if desired together with hydrogen gas, the amount of the methylating agent fed into each catalyst layer being 0.01/t moles to 1/t moles, in which t is the number of methyl groups in the methylating agent, per mole of toluene fed into the first-stage catalyst layer, and the total amount of the methylating agent fed into all of the catalyst layers being within the range of 0.1/t moles to 2/t moles, in which t is as defined, per mole of toluene fed into the first-stage catalyst layer, and (d) each fixed catalyst layer is filled with a catalyst composed of a crystalline aluminosilicate containing magnesium oxide or lanthanide oxide.

19 Claims, No Drawings

PROCESS FOR PRODUCING P-XYLENE

This invention relates to an improved process for producing p-xylene, and more specifically, to an industrially advantageous process for producing p-xylene by catalytically methylating toluene with a methylating agent in the gaseous phase.

Among various xylene isomers, p-xylene is by far the most useful compound in industrial applications because it can be converted to terephthalic acid or dimethyl terephthalate which is a starting material for polyesters. Industrially, p-xylene has been produced in quantities from a petrochemical fraction consisting mainly of $C_8$ aromatic hydrocarbons (so-called $C_8$ fraction) by separation and isomerization.

On the other hand, many processes involving alkylation of benzene or monoalkylbenzenes have recently been proposed for the production of dialkylbenzenes such as p-xylene.

For example, U.S. Pat. No. 4,117,026 issued on Sept. 26, 1978 discloses a process which comprises alkylating a $C_{1-4}$ monoalkylbenzene with a $C_{2-15}$ olefin and/or a $C_{3-60}$ paraffin in the presence of a catalyst composed of a certain kind of crystalline aluminosilicate. This process also embraces production of xylene and benzene by disproportionation of toluene itself. The proposed process, however, is not entirely satisfactory for industrial application in regard to the proportion of a p-dialkylbenzene in the dialkylbenzenes contained in the resulting reaction mixture, i.e. the selectivity of the p-dialkylbenzene.

U.S. Pat. No. 4,086,287 issued on Apr. 25, 1978 discloses a process for producing ethyltoluene or diethylbenzene which comprises ethylating toluene or ethylbenzene with an ethylating agent such as ethylene, ethyl alcohol, ethyl halides, or diethyl ether in the presence of a certain kind of crystalline aluminosilicate catalyst. This process is superior in that as compared with the prior processes, the amount of the ortho-di-substituted product is small and p-ethyltoluene or p-diethylbenzene is produced at a relatively high selectivity. However, it cannot be applied to the production of xylenes, above all p-xylene.

U.S. Pat. No. 3,965,207 issued on June 22, 1976 discloses a process for selective production of p-xylene which comprises methylating toluene at a temperature between about 500° C. and about 750° C. in the presence of a catalyst composed of a certain kind of crystalline aluminosilicate in which the silica/alumina mole ratio is at least about 12.

U.S. Pat. Nos. 4,034,053 issued on July 5, 1977 and 4,158,024 issued on June 12, 1979 disclose a process for producing p-xylene which comprises methylating toluene in the presence of a crystalline aluminosilicate modified with magnesium or its oxide. These processes are superior in that the proportion of p-xylene in the xylene isomers contained in the reaction mixture and the conversion of toluene to xylene are relatively high. With these processes, however, the concentration of p-xylene and the conversion of toluene achieved are not as high as are industrially satisfactory.

In the synthesis of p-xylene by methylation of toluene, the concentration of p-xylene in the xylene isomers and the conversion of toluene are of great industrial significance. In particular, the highest possible p-xylene concentration, desirably at least 85%, especially at least 90%, is a factor which determines the industrial value of a synthetic process.

The present inventors have already shown (see Japanese Laid-Open Patent Publication No. 144,324/1979) that when this methylation is carried out in the presence of a crystalline aluminosilicate catalyst for a shortened contact time to maintain the conversion of toluene low, a xylene isomeric mixture having a relatively high p-xylene concentration can be obtained as a reaction product, but that as the conversion of toluene is increased by prolonging the contact time, the concentration of p-xylene in the resulting xylene isomeric mixture tends to decrease. It would evidently be advantageous industrially if p-xylene can be produced from toluene with an industrially satisfactory high toluene conversion and p-xylene concentration. A manufacturing process which can realize it has therefore been strongly desired.

It is an object of this invention to provide an industrial process for producing a xylene mixture having a high p-xylene concentration by methylating toluene.

Another object of this invention is to provide an industrial process for producing a xylene mixture having a high p-xylene concentration with a high conversion of toluene.

Still another object of this invention is to provide an industrial process for producing p-xylene with a high conversion of the methylating agent to xylene.

Further objects and advantages of this invention will become apparent from the following description.

According to this invention, there is provided, in a process for producing p-xylene which comprises catalytically methylating toluene with a methylating agent in the gaseous phase, the improvement wherein (a) said methylation is carried out continuously in a multi-stage reaction system consisting of a plurality of separate series-connected fixed catalyst layers without separating the resulting xylenes in an intermediate stage, (b) said toluene is fed together with hydrogen gas into only the first-stage fixed catalyst layer and passed successively through the subsequent fixed catalyst layers, the amount of toluene fed being such that the total weight hourly space velocity of toluene is from 1 to 300 $hr^{-1}$, (c) said methylating agent is fed into each of said fixed catalyst layers, if desired together with hydrogen gas, the amount of the methylating agent fed into each catalyst layer being 0.01/t moles to 1/t moles, in which t is the number of methyl groups in the methylating agent, per mole of toluene fed into the first-stage catalyst layer, and the total amount of the methylating agent fed into all of the catalyst layers being within the range of 0.1/t moles to 2/t moles, in which t is as defined, per mole of toluene fed into the first-stage catalyst layer, and (d) each fixed catalyst layer is filled with a catalyst composed of a crystalline aluminosilicate containing magnesium oxide or lanthanide oxide.

To facilitate an understanding of the theory of the process in accordance with this invention, simple model experiments are described below. Specifically, two experiments are conducted.

(1) Toluene is methylated using a mixture of toluene and methanol in a certain ratio in the presence of a certain amount of a catalyst. (Experiment A in Example 2)

(2) The same catalyst as used in Experiment A is divided into two equal portions which are respectively filled in two separate series-connected catalyst layers. The same amount of toluene as used in Experiment A and methanol in an amount half as much as that used in Experiment A are fed into the first-stage catalyst layer. The remaining half of methanol is introduced into the reaction mixture discharged from the first-stage catalyst layer, and the reaction mixture is fed into the second-stage catalyst layer. In this way, methylation of toluene is carried out. (Experiment B in Example 2).

The temperature, the contact time and other conditions were maintained the same as much as possible for both the Experiments A and B. The results show that despite the same amounts of the catalyst, toluene and methanol used, Experiment B gives a higher conversion of toluene than Experiment A, and the concentration of p-xylene in the resulting xylene isomeric mixture is higher in Experiment B. It has also been found that the conversion of methanol consumed to xylene is improved in Experiment B.

Thus, by carrying out the methylation continuously in a multi-stage reaction system composed of a plurality of separate series-connected catalyst layers, the conversion of toluene can be easily increased, and the concentration of p-xylene in the resulting xylene isomeric mixture can be maintained high. In addition, the conversion of the methylating agent to xylene can be markedly increased. More specifically, according to the process of this invention, a xylene isomer mixture having a higher p-xylene concentration than in conventional processes involving the use of a single catalyst layer can be obtained at the same toluene conversion. Furthermore, when it is desired to obtain a xylene isomeric mixture having the same p-xylene concentration as in the conventional process, the reaction in accordance with this invention can be carried out at a higher conversion of toluene and a higher conversion of the methylating agent to xylene. These are the marked industrial advantages obtained by the present invention.

The invention is described in more detail below.

The basic feature of the present invention is that toluene is methylated while feeding the methylating agent to each of a plurality of separate series-connected fixed catalyst layers.

The catalyst constituting each of the fixed catalyst layers used in the process of this invention is composed of a crystalline aluminosilicate containing magnesium oxide or lanthanide oxide.

The crystalline aluminosilicate (to be sometimes referred to simply as "zeolite") as a base of the catalyst may be any of crystalline aluminosilicates which have been used in the catalytic methylation of toluene. Generally, there are used crystalline aluminosilicates which contain mainly hydrogen or a hydrogen precursor such as an ammonium ion at a cation site and have a silica/alumina mole ratio of at least 10, preferably from 15 to 5,000, more preferably from 20 to 3,000. In other words, a so-called high-silica zeolite having a high content of silica relative to alumina is used as a base of the catalyst. Many zeolites having a high silica content relative to alumina have been suggested heretofore, and a zeolite having an extremely high silica content represented by a silica/alumina mole ratio of as high as 5,000 is also known. Any known high-silica zeolites can be used in this invention if their silica/alumina mole ratio is within the above-specified range.

In addition, the crystalline aluminosilicate used in this invention has a crystal size within the range of generally 0.1 to 4 microns, preferably 0.15 to 3 microns more preferably 0.2 to 3 microns.

The catalyst used in this invention obtained by modifying the crystalline aluminosilicate advantageously has an alpha value, which reflects the relative activity of the zeolite, of generally 0.1 to 1,000, preferably 1 to 800, more preferably 5 to 600. The definition of the alpha value and a method for measuring it are described in Journal of Catalysis, 4, 527 (1965), and ibid., 6, 278 (1966). The measurement was performed in accordance with the method described in these literature references using the silica-alumina catalyst N631-HN of Nikki Chemicals Co.

The catalyst used in this invention obtained by modifying crystalline aluminosilicate preferably has relatively small pores. Advantageously, it has a weight ratio of cyclohexane to n-hexane sorptive capacity at 25° C. of generally in the range of 0.05 to 0.7, preferably in the range of 0.1 to 0.6, more preferably in the range of 0.2 to 0.6.

The expression "weight ratio of cyclohexane to n-hexane sorptive capacity at 25° C.", as used in the present specification and the appended claims, is defined as the ratio of the weight of cyclohexane adsorbed per unit weight of zeolite at 25° C. under a fixed hydrocarbon pressure to that of n-hexane adsorbed per unit weight of zeolite under the same conditions. The amounts of cyclohexane and n-hexane adsorbed are measured as follows: A fixed amount of the zeolite catalyst is weighed, and cyclohexane and n-hexane are caused to be as adsorbed to the zeolite catalyst to saturation at 25° C. and 120±20 mmHg for 6 hours. To remove adhering substances, the catalyst is kept further at 25° C. and 120±20 mmHg for 2 hours.

The weight ratio of cyclohexane to n-hexane sorptive capacity of zeolite ZSM-5 measured by this method is 0.7.

Typical examples of crystalline aluminosilicates or zeolites having the aforesaid properties which can be used in this invention as a base of the catalyst include various ZSM-series zeolites developed by Mobil Oil Corporation, and zeta-series zeolites developed by Impereal Chemical Industries, Ltd. The ZSM-zeolites are preferred.

Examples of ZSM-series zeolites are ZSM-5 (see U.S. Pat. No. 3,702,886), ZSM-11 (see U.S. Pat. No. 3,709,979), ZSM-12 (see U.S. Pat. No. 3,832,449), ZSM-35 (see U.S. Pat. No. 4,016,245) and ZSM-38 (see U.S. Pat. No. 4,046,859). Examples of zeta-series zeolites are zeta 1 (see German Offenlegungsschrift No. 2,548,697), and zeta 3 (see German Offenlegungsschrift No. 2,548,695).

TP-1 series zeolites discovered by the present inventors as high-silica zeolites (see Japanese Laid-Open Patent Publication No. 137,500/79) can also be used. These TP-1 series zeolites are obtained by heating a starting mixture containing silica, alumina, alkali metals and water at a temperature and for a time sufficient for the formation of crystalline aluminosilicates by using organic sulfur compounds such as thiols, sulfides, sulfoxides, sulfones or thiophenes. The properties of these TP-1 series zeolites and their production are described in detail in the specification of the Japanese Laid-Open Patent Publication cited above.

These zeolites are generally available in a form containing an alkali metal ion or an alkaline earth metal ion at the cation site. In the present invention, these zeolites are converted to H-form zeolites, and used in the form containing mainly hydrogen or a hydrogen precursor at the cation site. Accordingly, unless otherwise specified, "zeolite", as used in the present application, denotes H-form zeolite.

It has been found that the use of ZSM-5 zeolite as a base of catalyst produces the best effect. Thus, according to the most preferred embodiment of this invention, ZSM-5 zeolite is used as a base of the methylation catalyst.

The above zeolite is modified with magnesium oxide or lanthanide oxide, and then used in the process of this invention as a methylation catalyst. By modifying the zeolite with magnesium oxide or lanthanide oxide (to be sometimes referred to as "modifier A"), the concentration of p-xylene in the resulting xylene isomeric mixture, i.e. the selectivity of p-xylene, can be markedly increased.

The lanthanide oxide denotes an oxide of a lanthanide-type metal, such as lanthanum oxide, cerium oxide, ytterbium oxide, dysprosium, and neodymium oxide. Lanthanum oxide and cerium oxide are preferred.

Magnesium oxide and lanthanide oxide can be present singly or in a combination of two or more species on the zeolite.

The amounts of magnesium oxide and lanthanide oxide are not strictly limited, and can be varied widely depending upon the type of the zeolite to be modified, etc. Generally, the amount of magnesium oxide is 1 to 100% by weight, preferably 2 to 80% by weight, more preferably 5 to 50% by weight, based on the crystalline aluminosilicate, and the amount of the lanthanide oxide is 1 to 200% by weight, preferably 10 to 150% by weight, more preferably 20 to 100% by weight, based on the same basis.

The catalyst in accordance with this invention composed of the crystalline aluminosilicate modified with magnesium oxide or lanthanide oxide may further be modified with at least one metal (to be referred to as a "modifier B") selected from plantinum, rhodium and iridium. This modification can markedly prolong the life of the catalyst.

The above metal may exist at least partly in elemental form on the zeolite during the use of the catalyst, but the remainder may exist in the form of a metal oxide or other metal compound.

The amount of platinum, rhodium and/or iridium in the catalyst is not critical, but is generally 0.1 to 10% by weight, preferably 0.1 to 8% by weight, more preferably 0.1 to 5% by weight, calculated as metal based on the weight of the crystalline aluminosilicate.

According to this invention, the crystalline aluminosilicate modified with both magnesium oxide or lanthanide oxide and platinum, rhodium and/or iridium may further be modified with rhenium or metals of Group VIII of the periodic table other than platinum, rhodium and iridium or the oxides thereof (to be sometimes referred to as a "modifier C"). It has been found that this modification can lead to a striking increase in the conversion of toluene in the initial stage of the reaction by the aluminosilicate catalyst.

Examples of the metals of Group VIII other than platinum, rhodium and iridium include iron, cobalt, nickel, ruthenium, palladium and osmium.

The content of the modifier C in the catalyst may be varied widely. Generally, it can exist in an amount of 0.01 to 10% by weight, preferably 0.01 to 8% by weight, more preferably 0.01 to 5% by weight, based on the weight of the crystalline aluminosilicate.

The term "modified with a metal oxide or a metal" as used herein, means that the metal oxide or the metal is ion-exchanged at the cation site of zeolite and/or the metal oxide or the metal is physically deposited on the surface of zeolite.

A zeolite modified with the modifier A, a zeolite modified with modifiers A and B or a zeolite modified with modifiers A, B and C can be produced by methods generally known. For example, the zeolite modified with the modifier A, i.e. magnesium oxide or lanthanide oxide, can be prepared by the methods described in the above cited U.S. Pat. No. 4,034,053 and Japanese Laid-Open Patent Publication No. 144,323/1979. On the other hand, in the preparation of the zeolite modified with the modifiers A and B or the modifiers A, B and C, modifications by the modifiers A, B and C may be performed separately in any desired sequence, or simultaneously. In a preferred embodiment, modifications with the modifiers A and B are carried out simultaneously.

For easier understanding, typical examples of the modifying method are described below in detail.

Commercially available zeolites generally have alkali metal ions such as Na or K or alkaline earth metal ions such as Ca substituted at the cation site of the zeolites. Hence, the alkali or alkaline earth metal ion is exchanged with hydrogen or an ammonium ion. This exchange may be performed prior to the modification with the modifiers.

One method comprises dipping a zeolite having its cation site substituted with an alkali metal or alkaline earth metal ion in an aqueous solution containing an ammonium ion to give a zeolite product in which a greater portion of the cation site is of the ammonium ion form. Calcination of the resulting ammonium ion-form zeolite at a temperature of about 200° to 600° C. gives a hydrogen ion-form zeolite.

Another method comprises treating a zeolite having its cation site substituted with an alkali or alkaline earth metal ion with an inorganic or organic acid such as hydrochloric acid, sulfuric acid, nitric acid, acetic acid or oxalic acid to convert a greater portion of the cation site to a hydrogen ion form.

By the above methods, however, not all of the cation site of the zeolite can be converted to a hydrogen form, and generally a small amount of the original alkali or alkaline earth metal ion remains.

Modifications of zeolite with the modifier A (i.e. magnesium oxide or lanthanide oxide) and the modifier B (i.e., platinum, rhodium and/or iridium) can be performed in a customary manner simultaneously or separately by using a compound (to be referred to as a precursor A) capable of being converted to the modifier A by calcination in an oxygen atmosphere and a compound (to be referred to as a precursor B) capable of being converted to the metallic modifier B by calcination in a reducing atmosphere.

Specifically, in order to perform the modifications simultaneously, a zeolite to be treated is contacted with an aqueous or non-aqueous medium containing the desired precursor A and precursor B dissolved therein. For example, in modifying the zeolite with the modifier A (magnesium oxide) and the modifier B (platinum), the zeolite may be impregnated with a mixed aqueous solution of a water-soluble precursor A (such as magnesium nitrate hexahydrate) and water-soluble precursor B (such as $H_2PtCl_6.6H_2O$), and then the water is evaporated off to deposit the precursor A and the precursor B on the zeolite.

When the modifications are to be performed separately, a zeolite modified with the modifier A by the methods described in U.S. Pat. No. 4,034,053 and Japanese Laid-Open Patent Publication No. 144,323/1979 is impregnated in an aqueous or non-aqueous solution of the precursor B, and then the solvent is evaporated off to deposit the precursor B on the zeolite modified with the modifier A.

The zeolite having the precursor A and precursor B or modifier A and precursor B deposited thereon may be heated in an oxygen-containing atmosphere such as air at a temperature of 100° to 700° C., preferably 200° to 600° C., for about 1 to about 24 hours.

In use, the zeolite modified in the above-mentioned manner is treated in a reducing atmosphere such as hydrogen gas at a temperature of 200° to 600° C., preferably 250° to 550° C. This treatment is usually carried out after the catalyst has been filled in a reactor.

In this manner, the zeolite can be modified with the modifiers A and B.

In modifying a zeolite with the modifier A (i.e., magnesium oxide or lanthanide oxide), the modifier B (i.e., platinum, rhodium and iridium) and the modifier C (i.e., iron, cobalt, nickel, ruthenium, osmium, palladium or rhenium), the zeolite is impregnated with an aqueous or non-aqueous solution of a mixture of the precursor A, precursor B and a compound containing the modifier C (to be referred to as a precursor C), and then the solvent is evaporated off to deposit the precursor A, precursor B and precursor C on the zeolite, in the same way as in the modification with the modifiers A and B. Alternatively, the zeolite modified with the modifiers A and B by the method described above is impregnated in an aqueous or non-aqueous solution containing the precursor C and then the solvent is evaporated off to deposit the precursor C on the zeolite modified with the modifiers A and B. Then, the zeolite is calcined in an oxygen-containing atmosphere at a temperature of 100° to 700° C., preferably 200° to 600° C.

In use, the zeolite modified in the above-mentioned manner is treated in a reducing atmosphere such as hydrogen gas at a temperature of 100° to 700° C., preferably 250° to 550° C. This treatment is usually carried out after the catalyst has been filled in a reactor.

In this manner, the zeolite can be modified with the modifiers A, B and C.

Examples of the precursor A, precursor B and precursor C used to modify zeolites are given below. These examples are merely illustrative, and it should be understood that any water-soluble or solvent-soluble compounds of the respective modifiers can be equally used even if they are not specifically exemplified herein. Such compounds include the halides, oxides, sulfides, oxy acid salts, and complexes.

(1) Magnesium compounds
Magnesium nitrate, magnesium acetate and magnesium chloride.
(2) Lanthanum compounds
Lanthanum nitrate, lanthanum sulfate and lanthanum trichloride.
(3) Cerium compounds
Cerium nitrate and cerium sulfate.
(4) Dysprosium compounds
Dysprosium nitrate and dysprosium sulfate.
(5) Ytterbium compounds
Ytterbium nitrate and ytterbium sulfate.
(6) Platinum compounds
Hexachloroplatinic acid, platinum dichloride and tetraammine platinum dichloride.
(7) Rhodium compounds
Rhodium trichloride
(8) Iridium compounds
Iridium tetrachloride
(9) Iron compounds
Ferric nitrate and ferrous nitrate
(10) Cobalt compounds
Cobalt nitrate
(11) Nickel compounds
Nickel nitrate, nickel sulfate and nickel dichloride
(12) Ruthenium compounds
Ruthenium trichloride and ruthenium oxide
(13) Osmium compounds
Osmic acid and osmium tetrachloride
(14) Palladium compounds
Palladium dichloride, palladium sulfate, palladium nitrate, and tetraammine palladium dichloride.
(15) Rhenium compounds
Rhenium oxide and rhenium trichloride.

The resulting modified zeolite can be used in the methylation reaction either in the form of a fine powder, or after optionally shaping it into the various desired shapes such as pellets or tablets as in the case with the customary practice. A shaped article of the modified zeolite can be obtained in a customary manner by mixing the modified zeolite with a synthetic or natural refractory inorganic oxide usually employed as a binder for zeolite catalysts, such as silica, alumina, silica-alumina, kaolin or silica-magnesia, shaping the mixture into the desired configuration, and then calcining the shaped article. Advantageously, the amount of the modified zeolite as an active catalyst ingredient in the shaped article is generally 1 to 99% by weight, preferably 10 to 90% by weight, based on the weight of the shaped article.

The catalysts so prepared are used to form a plurality of separate series-connected fixed catalyst layers either singly or in combination in accordance with the process of this invention. In this case, the entirety of a reactor filled with the catalyst may be regarded as one catalyst layer unit. Or the reactor is divided into sections, and each section filled with the catalyst may be regarded as one catalyst layer unit.

Whichever catalyst layer unit is employed, the catalyst layer units are connected in series to each other so that a gas fed into the first-stage catalyst layer passes successively through the subsequent catalyst layers. Connection of the catalyst layers is effected such that in transferring the reaction mixture from one catalyst layer to the next, the resulting xylenes are not separated from the reaction mixture in an intermediate stage but the reaction mixture discharged from the catalyst layer in the previous stage, either directly or upon addition of a predetermined amount of a methylating agent, is fed into the catalyst layer in the next stage, and the resulting xylenes are separated and recovered only from the reaction mixture discharged from the final-stage catalyst layer.

The desired number of the fixed catalyst layers in the process of this invention is at least two. Although the effect achieved is greater as the number of the catalyst layers increases, it is virtually impossible to increase the number unlimitedly. Industrially, up to 20 catalyst layers are sufficient. Preferably, the number of the catalyst layers is in the range of 2 to 20, more preferably 4 to 20.

Desirably, the configuration of each catalyst layer is designed so as to secure D/L in which D is the diameter of the catalyst layer and L is the length of the catalyst layer required for the piston flow of a gas which passes through the catalyst layer. The catalyst molded in pellet or tablet form may be filled in a customary manner in the catalyst layer so designed.

The amount of the catalyst to be filled in each catalyst layer cannot be generalized because it depends largely upon the scale of a plant in which to perform the process of this invention, the size of the reactor, the weight hourly space velocity (WHSV for short) required for the toluene feed, etc. Those skilled in the art would be able to determine it easily from the disclosure of the present invention.

Desirably, the amount of the catalyst filled does not vary greatly from layer to layer. Generally, the amount (Wi) of the catalyst filled in the ith stage fixed catalyst layer satisfies the following inequality.

$$\frac{0.5}{n} \sum_{m=1}^{n} Wm < Wi < \frac{1.5}{n} \sum_{m=1}^{n} Wm \quad (1)$$

wherein Wi is the amount of the catalyst filled in the ith stage fixed catalyst layer, Wm is the amount of the catalyst filled in the mth stage fixed catalyst layer, and n is the number of catalyst layers used in the process of this invention. Advantageously, it should satisfy the following inequality.

$$\frac{0.8}{n} \sum_{m=1}^{n} Wm < Wi < \frac{1.2}{n} \sum_{m=1}^{n} Wm \quad (2)$$

wherein Wi, Wm, m and n are as defined.

Throughout the present specification and the appended claims, the term "amount of the catalyst filled" means the net weight of the catalytically active component of the catalyst excepting catalytically inert components such as a binder.

In the plurality of connected catalyst layers, toluene as a starting material is fed only into the first-stage catalysts layer together with hydrogen gas which serves to inhibit degradation of the activity of the carrier and to improve the performance of the reaction. The amount of toluene fed is not critical, and can be varied widely according to the scale of each catalyst layer, the performance of the filled catalyst, the reaction conditions, etc. Generally, the amount of toluene fed is advantageously controlled so that the total WHSV of toluene in the multi-stage reaction system in accordance with this invention is within the range of 1 to 300 hr$^{-1}$, preferably 2 to 200 hr$^{-1}$, more preferably 2 to 100 hr$^{-1}$.

The term "weight hourly space velocity (WHSV)", as used in the present specification and the appended claims, is defined as the weight in grams of a substance fed onto the catalyst per gram of the catalyst per hour.

The amount of the hydrogen gas fed into the first-stage catalyst layer is neither strictly limited, and can be varied widely depending upon the size of the catalyst layer, etc. Generally, the suitable amount of hydrogen gas is 0.5 to 20 moles, preferably 0.5 to 15 moles, more preferably 1 to 10 moles, per mole of toluene fed.

Toluene is gasified prior to feeding into the first-stage catalyst layer. At least a part of the hydrogen gas may be mixed with the gasified toluene and the mixture may be fed into the first-stage catalyst layer. Or a part, or the whole, of the hydrogen gas may be fed separately from toluene into the first-stage catalyst layer.

The methylating agent used in methylating toluene is fed into each of a series of fixed catalyst layers in accordance with the process of this invention.

The methylating agent may be any of compounds which have heretofore been used for the methylation of aromatic ring. Examples include methanol, methyl halides and dimethyl ether. Methanol, dimethyl ether and a mixture of these, particularly methanol or a mixture of methanol and dimethyl ether in a desired ratio, are preferred.

One purpose of the present invention is to increase the conversion of the methylating agent to xylene. To achieve this, the ratio of the amount of the methylating agent to that of toluene in each catalyst layer should desirably be maintained low. Theoretically, it is advantageous that the proportion of the methylating agent to be fed into each catalyst layer should be adjusted to not more than 1/t moles, preferably 0.02/t to 0.5/t moles, more preferably 0.02/t to 0.3/t moles, per mole of toluene fed into each catalyst layer. The letter t denotes the number of methyl groups in the methylating agent. With methanol and methyl halides, t equals 1. With dimethyl ether, t is 2. It is ideal to measure the amount of unreacted toluene in the reaction mixtures to be fed into the catalyst layers in the second and subsequent stages and to determine the amount of the methylating agent to be fed into each catalyst layer according to the results of measurement. This, however, is not practicable in industrial application because it is troublesome and the apparatus becomes complex.

Investigations of the present inventors have shown that the above purpose can be fully achieved by adjusting the amount of the methylating agent to be fed into each catalyst layer to 0.01/t to 1/t moles, preferably 0.02/t to 0.5/t moles, more preferably 0.02/t to 0.3/t moles, in which t is as defined hereinabove, per mole of toluene fed into the first-stage catalyst layer.

The total amount of the methylating agent fed into all of the catalyst layers should be 0.1/t to 2/t moles, preferably 0.1/t to 1.5/t moles, more preferably 0.1/t to 1/t moles, per mole of toluene fed into the first-stage catalyst layer.

Accordingly, the amount of the methylating agent to be fed into each catalyst layer may be selected freely from the aforesaid range so long as the total amount of the methylating agent is within the above-specified range. Desirably, the amount of the methylating agent fed does not vary greatly from layer to layer. Preferably, the amounts of the methylating agent fed into the catalyst layers are substantially the same, or increase progressively from the first to the last stages. Desirably, the amount (Qi) of the methylating agent to be fed into the ith stage catalyst layer satisfies the following inequality $$\frac{1}{t} \geq Qi \geq \frac{1}{i-1} \sum_{m=1}^{i-1} Qm \quad (3)$$

wherein Qi is the amount in moles of the methylating agent fed into the ith stage catalyst layer per mole of toluene fed into the first-stage catalyst layer, and Qm is the amount in moles of the methylating agent fed into the mth stage catalyst layer per mole of the toluene fed into the first-stage catalyst layer.

Advantageously, it satisfies the following inequality $$\frac{0.5}{t} \geqq Qi \geqq \frac{1}{i-1} \sum_{m=1}^{i-1} Qm \quad (4)$$

wherein Qi, Qm and t are as defined above.

The methylating agent may be fed directly to each catalyst layer after it is gasified. Suitably, the methylating agent is fed into the first-stage catalyst layer as a mixture with toluene although it may be fed separately from toluene and hydrogen gas. It is convenient to feed a mixture of the methylating agent with the reaction mixture discharged from the previous stage catalyst layer into the second and subsequent catalyst layers. As a result, uniform mixing of the methylating agent and the reaction mixture to be fed into a certain specified catalyst layer can be achieved and this also serves to quench the reaction mixture.

The catalytic methylation of toluene is an exothermic reaction, and the reaction mixture discharged from the catalyst layer is at a considerably high temperature. If the temperature of the reaction mixture is considerably higher than the desired reaction temperature, it may, as required, be quenched to the desired reaction temperature by adding hydrogen gas together with the methylating agent to it.

Alternatively, either singly or in combination with the quenching by hydrogen gas, the quenching operation may be carried out by using a recycle gas left after the reaction mixture discharged from the final-stage catalyst layer is cooled and xylenes and the unreacted toluene, etc. are removed from it. The methylation conditions in each catalyst layer may be the same as those used in the above-described prior art. For example, the reaction temperature in each catalyst layer is generally 250° to 700° C., preferably 300° to 600° C., and the reaction pressure is 1 to 20 atmospheres, preferably 1 to 15 atmospheres.

Xylenes may be recovered in a manner known per se from the reaction mixture discharged from the final-stage catalyst layer. For example, the reaction mixture is fully cooled by a product cooler, and condensed by a gas/liquid separator, e.g. a debutanizer, to separate the oil-water mixture from the gas. The oil-water mixture is separated, and the oil is fed into a distillation column where the unreacted toluene, xylenes and other by-products are separated. Thus, xylenes can be easily recovered.

The used catalyst having reduced activity in the process of this invention can be re-used after it is regenerated. The regeneration of the catalyst can be effected easily, for example by isolating the reactor, purging flammable gases, heating the reactor while passing an inert gas such as nitrogen, then adding air capable of controlling the temperature of the catalyst bed to remove the carbonaceous compound deposited on the catalyst, and finally heating the catalyst bed to 500° to 550° C.

According to the process of this invention, very high conversions of toluene and the methylating agent to xylene can be achieved, and at the same time, a high p-xylene concentration in the resulting xylene isomeric mixture, i.e. high p-xylene selectivity, can be obtained, as will be clearly seen from Examples given hereinbelow. According to the process of this invention, under preferred conditions, the conversion of toluene reached at least 10%, usually 20 to 60%, and the concentration of p-xylene in the resulting xylene isomeric mixture is much higher than the heretofore known thermodynamic composition value, for example at least 70%, usually 80 to 95%.

Furthermore, since each catalyst layer used in the process of this invention is made up of a fix-bed catalyst layer, the contact time can be varied as desired, and the temperature of the present reaction which is exothermic can be easily controlled by introducing a quenching gas into each catalyst layer.

As stated hereinabove, since a plurality of catalyst layers are used in this invention. The operation of regeneration of the used catalyst can be simplified.

The process of this invention is specifically described below in accordance with a flow used in industrial practice. For example, toluene is set at a desired charge rate by means of a charge pump. A hydrogen-containing gas (to be referred to as a recycle gas) obtained by raising the pressure of a gas separated by a gas-liquid separator or debutanizer by using a recycle gas compressor is mixed with toluene. The mixed flow is heated successively by a feed-effluent heat-exchanger and a furnace in this order. The methylating agent whose temperature and pressure have been adjusted in advance is mixed with the toluene-containing recycle gas kept at the desired temperature. The mixture is fed as a down flow into a fixed bed-type reactor. The fixed bed-type reactor may consist of one reactor whose inside is divided into a plurality of catalyst layers, or of a plurality of reactors at least one of which is further divided into a plurality of catalyst layers. A thermocouple for measuring the temperature of each of the catalyst layers is provided to control the reaction temperature easily (control the regenerating conditions in the case of regenerating the used catalyst).

Desirably, nozzles for feeding the methylating agent and the recycle gas required for quenching are set up in a passage for feeding the reaction mixture from the first-stage catalyst layer to the second-stage catalyst layer in order to mix the reaction mixture from the first-stage catalyst layer completely with the methylating agent and the quenching gas. A distributor at the inlet of the catalyst layer and a collector at its outlet may be used.

Devices for introducing the methylating agent and the quenching gas are provided between the catalyst layers to feed the desired methylating agent and quenching gas. The amount of the quenching gas can be determined in relation to the indicated value on the thermocouple provided in the reactor.

The reaction mixture which has left the final stage catalyst layer is cooled with a feed-effluent heat exchanger, and then passed through a cooler. A mixed flow of the condensate and the gas is introduced into a gas-liquid separator (e.g., a debutanizer).

A part of the gas separated by the gas-liquid separator is compressed by a recycle gas compressor to increase its pressure. The compressed gas is partly mixed with toluene and partly used as a quenching gas. The remainder of the gas is discharged out of the unit.

If the hydrogen/toluene mole ratio is lower than the desired value, hydrogen make-up is necessary before or after the recycle gas compressor.

When the methylating agent is an oxygen-containing compound, water may sometimes be separated in the gas-liquid separator. In this case, a device is desirably installed for separation of the oil-water mixture.

The oil layer condensed by the gas-liquid separator is fed into a topping still where toluene and xylenes are mainly separated. A condensate consisting predominantly of toluene and gases is separated from the topping overhead. The condensate consisting predominantly of toluene may be used directly as a charge stock for methylation. Or it is possible to separate a lighter fraction and charge the resulting fraction consisting mostly of toluene into the methylation unit. The bottom fraction of the topping still is fed to a xylene splitter and where it can be separated into xylenes and $C_9{}^+$ aromatics. The xylenes are fed into a p-xylene separation unit, and finally commercial p-xylene is obtained.

Separation of p-xylene may be effected, for example, by a so-called p-xylene adsorption process using a molecular sieve, or a p-xylene crystallization process.

The concentration of p-xylene in the stream to be subjected to the p-xylene separating process is about 20% by weight in accordance with a usual method. But in accordance with this invention, it is at least about 70% by weight. It will be readily understood that this reflects a striking improvement in the efficiency of the apparatus used for separation of p-xylene.

The following Examples illustrate the process of this invention more specifically.

EXAMPLE 1

Zeolite ZSM-5 (to be referred to simply as ZSM-5) was synthesized in accordance with the procedure set forth in Example 1 of U.S. Pat. No. 3,965,207. ZSM-5 was calcined in the air at 500° C. for 16 hours. Twenty grams of ZSM-5 was subjected to ion exchange with 200 cc of a 1 M solution of $NH_4Cl$ at 80° C. for 24 hours. The product was fully washed with water, dried at 100° C., and then calcined in the air at 500° C. for 16 hours. This H-form ZSM-5 had a crystal size within the range of 0.1 to 2 microns, a silica/alumina mole ratio of 65, an alpha value of at least 10,000, a weight ratio of cyclohexane to n-hexane sorptive capacity at 25° C. of 0.7, and a residual alkali and alkaline earth metal content of 0.01% by weight. The above alpha value was obtained by comparing the activity of ZSM-5 at 540° C., which was calculated by measuring the activities at a temperature of 200° to 250° C. and hypothesizing that the activation energy equals 30 kcal/mole, with the activity of the silica-alumina catalyst N.631-HN of Nikki Chemicals Co. at 540° C.

Synthesis of catalyst A 0.5 g of the H-form ZSM-5 powder was suspended in a solution of 0.64 g of $Mg(NO_3)_2.6H_2O$ in 10 ml of water. While heating the suspension at 80° C., it was allowed to stand overnight. Then, water was evaporated off by using an evaporator for 4 hours. The product was then calcined at 500° C. for 16 hours in an air atmosphere to give a catalyst A modified with MgO. The catalyst contained 20.0% by weight of magnesium and/or its oxide based on the weight of the H-form ZSM-5. The calcined product was molded and pulverized to a size of 10 to 20 mesh. The catalyst had an alpha value of 60 and a weight ratio of cyclohexane to n-hexane sorptive capacity at 25° C. of 0.44.

Synthesis of catalyst B

Substantially in accordance with the procedure for synthesizing the catalyst A, a catalyst B containing 5.0% by weight of magnesium and/or its oxide was prepared.

Synthesis of a catalyst C 0.5 g of the H-form ZSM-5 powder was suspended in a solution of 0.50 g of $La(NO_3)_3.6H_2O$ in 10 ml of water. While heating the suspension at 80° C., it was allowed to stand overnight. Then, water was evaporated off. The product was then calcined in the air at 500° C. for 16 hours to give a catalyst C modified with $La_2O_3$ and containing 37.6% by weight, based on the weight of the H-form ZSM-5, of lanthanum and/or its oxide. The calcined product was molded and pulverized to a size of 10 to 20 mesh.

Synthesis of catalyst D

Substantially in accordance with the procedure for preparing the catalyst C, a catalyst D containing 20.2% by weight of lanthanum and/or its oxide was synthesized.

Synthesis of catalyst E

A catalyst E containing 39.4% by weight of dysprosium and/or its oxide was synthesized in accordance with the procedure for synthesizing the catalyst C except that 0.46 g of $Dy(NO_3)_3.5H_2O$ was used instead of the lanthanum nitrate.

Synthesis of catalyst F

A catalyst F containing 37.1% by weight of cerium or its oxide was synthesized in the same way as in the procedure for synthesizing the catalyst C except that 0.49 g of $Ce(NO_3)_3.6H_2O$ was used instead of the lanthanum nitrate.

Synthesis of catalyst G

A catalyst G containing 40.4% by weight of ytterbium and/or its oxide was synthesized in the same way as in the procedure of synthesizing the catalyst C except that 0.44 g of $Yb(NO_3)_2.4H_2O$ was used instead of the lanthanum nitrate.

Synthesis of catalyst H 0.5 g of the H-form ZSM-5 powder was suspended in a solution of 0.16 g of $Mg(NO_3)_2.6H_2O$ and 6.63 mg of $H_2PtCl_6.6H_2O$ in 10 ml of water. While heating the suspension at 80° C., it was allowed to stand overnight. Then, water was evaporated off. The product was calcined in an atmosphere of air at 500° C. for 16 hours. The calcined product was molded and pulverized to a size of 10 to 20 mesh to give a catalyst H.

Synthesis of catalyst I

A catalyst I was prepared in the same way as in the synthesis of the catalyst H except that a solution of 0.27 g of $La(NO_3)_3.6H_2O$ and 6.63 mg of $H_2PtCl_6.6H_2O$ in 10 ml of water was used instead of the solution of magnesium nitrate and hexachloroplatinic acid.

Synthesis of catalyst J

A catalyst J was prepared in the same way as in the synthesis of the catalyst H except that a solution of 0.16 g of $Mg(NO_3)_2.6H_2O$ and 6.41 mg of $RhCl_3.3H_2O$ in 10 ml of water was used instead of the solution of magnesium nitrate and hexachloroplatinic acid.

Synthesis of catalyst K 0.5 g of the ZSM-5 powder was suspended in a solution of 0.16 g of $Mg(NO_3)_2.6H_2O$ and 4.34 mg of $IrCl_4$ in 10 ml of water. The suspension was allowed to stand overnight at room temperature, and then water was evaporated off. The product was calcined in an atmosphere of air at 500° C. for 16 hours. The calcined product was molded and pulverized to a size of 10 to 20 mesh to form a catalyst K.

Synthesis of catalyst L 0.5 g of the H-form ZSM-5 powder was suspended in a solution of 0.16 g of $Mg(NO_3)_2.6H_2O$, 6.63 mg of $H_2PtCl_6.6H_2O$ and 2.13 mg of $IrCl_4$ in 10 ml of water. The suspension was allowed to stand at room temperature overnight, and then water was evaporated off. Then, the product was calcined in an atmosphere of air at 500° C. for 16 hours. The calcined product was molded and pulverized to a size of 10 to 20 mesh to give a catalyst L.

Synthesis of catalyst M 0.5 g of the H-form ZSM-5 powder was suspended in a solution of 0.16 g of $Mg(NO_3)_2.6H_2O$, 6.63 mg of $H_2PtCl_6.6H_2O$ and 1.86 mg of $Ni(NO_3)_2.6H_2O$. The suspension was allowed to stand at 80° C. overnight, and then water was evaporated off. The product was then calcined in an atmosphere of air at 500° C. for 16 hours. The calcined product was molded and pulverized to a size of 10 to 20 mesh to form a catalyst M.

EXAMPLE 2

A multi-stage fixed bed flowing-type reaction apparatus was used which had ten catalyst layers and reaction tubes for material supply to the catalyst layers.

Experiment A 2.0 g of the catalyst A was filled in the first-stage catalyst layer, and toluene and methanol were fed into the first-stage catalyst layer at a ratio of 20.0 g/hr and 3.5 g/hr respectively at 500° C. and atmospheric pressure.

Experiment B 1.0 g of the catalyst A was filled in each of the first-stage and second-stage catalyst layers in the aforesaid reaction apparatus. Under atmospheric pressure at 500° C., toluene and methanol were fed into the first-stage catalyst layer at a ratio of 20 g/hr and 1.75 g/hr respectively, and methanol was fed into the second-stage catalyst layer at a rate of 1.75 g/hr.

The results of Experiments A and B are given in Table 1. The results show that Experiment B was superior to Experiment A in regard to toluene conversion, p-xylene selectivity, methanol selectivity and xylene yield.

The toluene conversion, p-xylene selectivity, methanol selectivity and xylene yield are defined by the following equations in all of the Examples.

$$\text{Toluene conversion (\%)} = \frac{\text{Moles of toluene converted}}{\text{Moles of toluene fed}} \times 100$$

$$\text{p-Xylene selectivity (\%)} = \frac{\text{Moles of p-xylene formed}}{\text{Moles of xylenes formed}} \times 100$$

$$\text{Methanol selectivity (\%)} = \frac{\text{Moles of xylenes formed}}{\text{Moles of methanol fed}} \times 100$$

$$\text{Xylene yield (\%)} = \frac{\text{Moles of xylenes formed}}{\text{Moles of toluene converted}} \times 100$$

TABLE 1

| Experiment | A | B |
| --- | --- | --- |
| Toluene conversion (%) | 15.5 | 16.5 |
| p-Xylene selectivity (%) | 80.0 | 84.5 |
| Methanol selectivity (%) | 27.7 | 29.8 |
| Xylene yield (%) | 89.4 | 90.4 |

(*) Time on stream 1 hr.

EXAMPLE 3

Using the same reaction apparatus as used in Example 2 the following experiments A to D were conducted. The reaction was carried out at 500° C. under atmospheric pressure in all runs. In Experiments A to D, the mole ratio of total methanol to toluene was maintained at 1:2.

Experiment A 1.0 g of the catalyst A was filled in the first-stage catalyst layer, and a mixture of methanol and toluene in a mole ratio of 1:2 was fed into the first-stage catalyst layer at a WHSV of 10 to 100 $hr^{-1}$.

Experiment B 1.0 g of the catalyst A was filled in each of the first-stage and second-stage catalyst layers. A mixture of methanol and toluene in a mole ratio of 1:4 was fed into the first-stage catalyst layer at a WHSV of 10 to 100 $hr^{-1}$, and the same amount of methanol as that fed into the first-stage layer was fed into the second-stage catalyst layer.

Experiment C 1.0 g of the catalyst was filled in each of the first-stage to fifth-stage catalyst layers. A mixture of methanol and toluene at a mole ratio of 1:10 was fed into the first-stage catalyst layer at a WHSV of 10 to 100 $hr^{-1}$. The same amount of methanol as that fed into the first-stage layer was fed into each of the second-stage to fifth-stage catalyst layers.

Experiment D 1.0 g of the catalyst A was filled in each of the first-stage to tenth-stage catalyst layers. A mixture of methanol and toluene at a mole ratio of 1:20 was fed into the first-stage catalyst layer at a WHSV of 10 to 100 $hr^{-1}$, and the same amount of methanol as fed to the first-stage layer was fed into each of the second-stage to tenth-stage catalyst layers.

WHSV, as used in this and other Examples, denotes the amount of toluene fed per hour per gram of catalyst.

Tables 2 and 3 below summarize the toluene conversion, methanol selectivity and xylene yield obtained when the concentration of p-xylene in the resulting xylene isomeric mixture was about 80%, and about 85%, respectively.

TABLE 2

| Experiment | Number of catalyst layers | WHSV ($hr^{-1}$) | p-Xylene selectivity (%) | Toluene conversion (%) | Methanol selectivity (%) | Xylene yield (%) |
| --- | --- | --- | --- | --- | --- | --- |
| A | 1 | 10.2 | 79.5 | 15.0 | 26.7 | 89.0 |
| B | 2 | 8.1 | 80.2 | 16.8 | 30.7 | 91.4 |
| C | 5 | 6.8 | 80.3 | 19.7 | 36.0 | 91.4 |
| D | 10 | 6.7 | 79.8 | 19.8 | 37.2 | 93.9 |

(*) Time on stream: 1 hour

TABLE 3

| Experiment | Number of catalyst layers | WHSV (hr⁻¹) | p-Xylene selectivity (%) | Toluene conversion (%) | Methanol selectivity (%) | Xylene yield (%) |
|---|---|---|---|---|---|---|
| A | 1 | 14.9 | 85.2 | 13.2 | 24.0 | 91.6 |
| B | 2 | 10.1 | 85.5 | 16.0 | 29.7 | 92.8 |
| C | 5 | 9.7 | 84.9 | 17.6 | 32.9 | 93.5 |
| D | 10 | 8.4 | 85.0 | 18.0 | 36.9 | 94.6 |

(*) Time on stream: 1 hour

Table 4 summarizes the p-xylene selectivity, methanol selectivity and xylene yield in Experiments A to D when the toluene conversion was about 16%.

TABLE 4

| Experiment | Number of catalyst layers | WHSV (hr⁻¹) | Toluene conversion (%) | p-Xylene selectivity (%) | Methanol selectivity (%) | Xylene yield (%) |
|---|---|---|---|---|---|---|
| A | 1 | 7.4 | 16.0 | 77.0 | 28.5 | 89.0 |
| B | 2 | 10.1 | 16.2 | 85.0 | 29.7 | 92.8 |
| C | 5 | 10.9 | 15.7 | 87.0 | 30.4 | 95.0 |
| D | 10 | 12.6 | 15.9 | 90.0 | 30.6 | 95.6 |

(*) Time on stream: 1 hour

The results given in Tables 2 to 4 demonstrate that as a result of using a multiplicity of catalyst layers, the selectivity of p-xylene at the same toluene conversion can be increased, and to obtain a xylene mixture of the same p-xylene selectivity, a higher toluene conversion and a higher methanol selectivity can be attained.

EXAMPLE 4

1.0 g of the catalyst B was filled in each of the first-stage to fifth-stage catalyst layers of the same reaction apparatus as used in Example 2. A mixture of methanol and toluene in a mole ratio of 1:10 was fed into the first-stage catalyst layer at a WHSV of 10 to 200 hr⁻¹, and the same amount of methanol as that fed into the first-stage layer was fed into each of the second-stage to fifth-stage catalyst layers. The reaction was carried out at 500° C. under atmospheric pressure. The results are shown in Table 5.

TABLE 5

| WHSV (hr⁻¹) | 9.5 | 16 | 22 | 31 |
|---|---|---|---|---|
| Toluene conversion (%) | 23.0 | 20.0 | 16.8 | 12.0 |
| p-Xylene selectivity (%) | 70.0 | 80.0 | 85.0 | 90.0 |
| Methanol selectivity (%) | 37.3 | 33.3 | 28.5 | 20.8 |
| Xylene yield (%) | 81.0 | 83.2 | 85.0 | 86.5 |

(*) Time on stream: 1 hour

EXAMPLE 5

1.0 g of the catalyst C was filled in the first-stage to fifth-stage of the same reaction apparatus as used in Example 2. A mixture of methanol and toluene in a mole ratio of 1:10 was fed into the first-stage catalyst layer at a WHSV of 100 to 2,000 hr⁻¹, and the same amount of methanol as that fed into the first-stage catalyst layer was fed into each of the second-stage to fifth stage catalyst layers. The reaction was carried out at 500° C. under atmospheric pressure. The results are shown in Table 6.

TABLE 6

| WHSV (hr⁻¹) | 32 | 65 | 155 | 309 |
|---|---|---|---|---|
| Toluene conversion (%) | 26.1 | 23.9 | 19.0 | 13.8 |
| p-Xylene selectivity (%) | 61.5 | 75.1 | 84.1 | 87.5 |
| Methanol selectivity (%) | 48.7 | 45.2 | 36.9 | 26.9 |
| Xylene yield (%) | 93.2 | 94.5 | 97.1 | 97.5 |

(*) Time on stream: 1 hour

The results given in Tables 5 and 6 demonstrate that the p-xylene selectivity can be increased by increasing WHSV, and the toluene conversion, and methanol selectivity can be increased by decreasing WHSV.

EXAMPLE 6

1.0 g of the catalyst A was filled in each of the first-stage and second-stage catalyst layers of the same reaction apparatus as used in Example 2. At 500° C. under atmospheric pressure, a mixture of methanol and toluene in a mole ratio of from 1:20 to 1:1 was fed into the first-stage catalyst layer at a WHSV of 25, and the same amount of methanol as that fed into the first-stage catalyst layer was fed into the second-stage catalyst layer. The results are shown in Table 7.

TABLE 7

| Methanol/toluene mole ratio | Toluene conversion (%) | p-Xylene selectivity (%) | Methanol selectivity (%) | Xylene yield (%) |
|---|---|---|---|---|
| 2.0 | 19.2 | 88.0 | 8.9 | 93.0 |
| 1.0 | 18.0 | 88.0 | 16.7 | 93.2 |
| 0.5 | 15.0 | 88.0 | 27.9 | 92.8 |
| 0.20 | 9.5 | 87.0 | 44.2 | 92.5 |
| 0.10 | 6.0 | 85.5 | 55.8 | 93.1 |

(*) Time on stream: 1 hour

EXAMPLE 7

1.0 g of the catalyst A was filled in each of the first-stage to tenth-stage catalyst layers of the same reaction apparatus as used in Example 2. At 500° C. under atmospheric pressure, a mixture of methanol and toluene in a mole ratio of from 1:20 to 1:4 was fed into the first-stage catalyst layer at a WHSV of 25, and the same amount of methanol as that fed into the first-stage catalyst layer was fed into each of the second-stage to tenth-stage catalyst layers. The results are summarized in Table 8.

TABLE 8

| Methanol/toluene mole ratio | Toluene conversion (%) | p-Xylene selectivity (%) | Methanol selectivity (%) | Xylene yield (%) |
|---|---|---|---|---|
| 2.5 | 42.5 | 76.0 | 15.5 | 91.0 |
| 1.0 | 34.5 | 66.0 | 31.4 | 91.2 |
| 0.5 | 23.5 | 61.5 | 40.8 | 91.1 |

(*) Time on stream: 1 hour

The results given in Tables 7 and 8 demonstrate that the toluene conversion can be increased by increasing the methanol/toluene mole ratio, and the methanol selectivity can be increased by decreasing the methanol/toluene mole ratio.

EXAMPLE 8

1.0 g of the catalyst A was filled in each of the first-stage and second-stage catalyst layers of the same reaction apparatus as used in Example 2. At 500° C. under atmospheric pressure, a mixture of methanol and toluene in a mole ratio of 1:4 was fed into the first-stage catalyst layer at a WHSV of 23, and the same amount of methanol as fed to that fed into the first-stage catalyst layer was fed into the second-stage catalyst layer. The results are shown in Table 9.

TABLE 9

| H₂/toluene mole ratio | 0 | 1.5 | 3.0 | 6.0 | 8.75 |
|---|---|---|---|---|---|
| Toluene conversion (%) | 20.6 | 19.6 | 19.0 | 18.9 | 18.7 |
| p-Xylene selectivity (%) | 81.2 | 91.0 | 93.1 | 92.1 | 92.3 |
| Methanol selectivity (%) | 35.3 | 36.1 | 36.1 | 35.6 | 35.5 |
| Xylene yield (%) | 85.5 | 92.2 | 94.8 | 94.4 | 95.0 |

(*) Time on stream: 1 hour

Table 9 shows that by using hydrogen as a carrier, the p-xylene selectivity, methanol selectivity and xylene yield can be increased.

EXAMPLE 9

1.0 g of the catalyst A was filled in the first-stage and second-stage catalyst layers of the same reaction apparatus as used in Example 2. At 500° C. under atmospheric pressure, a mixture of methanol and toluene in a mole ratio of 1:4 was fed into the first-stage catalyst layer at a WHSV of 23, and the same amount of methanol as that fed into the first-stage catalyst layer was fed into the second-stage catalyst layer. Furthermore, hydrogen in an amount three molar times the amount of the toluene fed was supplied dividedly into the first-stage and second-stage catalyst layers. The results are shown in Table 10.

TABLE 10

| 1st/2nd stage charge hydrogen ratio | 16/84 | 50/50 | 84/16 | 100/0 |
|---|---|---|---|---|
| Toluene conversion (%) | 18.6 | 18.6 | 18.4 | 19.0 |
| p-Xylene selectivity (%) | 88.4 | 90.8 | 91.8 | 93.1 |
| Methanol selectivity (%) | 34.4 | 34.9 | 35.1 | 36.1 |
| Xylene yield (%) | 92.3 | 93.8 | 95.7 | 94.8 |

(*) Time on stream: 1 hour

Table 10 shows that the greatest possible portion of hydrogen as a carrier is preferably fed into the first-stage catalyst layer.

EXAMPLE 10

1.0 g of the catalyst A was filled in each of the first-stage and second-stage catalyst layers of the same reaction apparatus as used in Example 2. At 500° C. under atmospheric pressure, toluene was fed at a WHSV of 23 into the first-stage catalyst layer. Methanol in an amount corresponding to one half of the amount in moles of toluene fed into the first-stage layer was fed dividedly into the first-stage and second-stage catalyst layers. The results are shown in Table 11.

TABLE 11

| 1st/2nd stage charge methanol ratio | 10/90 | 30/70 | 50/50 | 70/30 | 90/10 |
|---|---|---|---|---|---|
| Toluene conversion (%) | 15.4 | 18.1 | 16.5 | 15.0 | 12.8 |
| p-Xylene selectivity (%) | 90.8 | 88.1 | 86.4 | 85.5 | 84.8 |
| Methanol selectivity (%) | 27.5 | 32.2 | 29.2 | 26.2 | 22.2 |
| Xylene yield (%) | 89.4 | 89.1 | 88.4 | 87.4 | 86.9 |

(*) Time on stream: 1 hour

EXAMPLE 11

1.0 g of the catalyst A was filled in each of the first-stage to third-stage catalyst layers of the same reaction apparatus as used in Example 2. At 500° C. under atmospheric pressure, toluene was fed into the first-stage catalyst layer at a WHSV of 23, and methanol in an amount corresponding to one half of the amount in moles of toluene fed was dividedly fed into each of the first-stage to third-stage catalyst layers. The results are shown in Table 12.

TABLE 12

| 1st/2nd/3rd stage charge methanol ratio | 16/34/50 | 33/34/33 | 50/34/16 |
|---|---|---|---|
| Toluene conversion (%) | 18.5 | 19.2 | 18.3 |
| p-Xylene selectivity (%) | 84.7 | 81.3 | 78.9 |
| Methanol selectivity (%) | 31.5 | 31.8 | 29.9 |
| Xylene yield (%) | 85.2 | 83.0 | 81.9 |

(*) Time on stream: 1 hour

The results given in Tables 11 and 12 show that the amount of the methylating agent is preferably increased progressively from the first-stage catalyst layer to the last-stage catalyst layer.

EXAMPLE 12

0.8 g of the catalyst A was dividedly filled into the first-stage and second-stage catalyst layers of the same reaction apparatus as used in Example 2. At 500° C. under atmospheric pressure, toluene and methanol were fed into the first-stage catalyst layer at a rate of 9.21 g/hr and 0.80 g/hr respectively, and methanol was fed into the second-stage catalyst layer at a rate of 0.80 g/hr. The results are shown in Table 13.

TABLE 13

| 1st/2nd stage catalyst loading ratio | 25/75 | 50/50 | 75/25 |
|---|---|---|---|
| Toluene conversion (%) | 13.8 | 16.5 | 14.5 |
| p-Xylene selectivity (%) | 82.6 | 86.4 | 86.1 |
| Methanol selectivity (%) | 24.2 | 29.2 | 25.5 |
| Xylene yield | 87.9 | 88.5 | 87.7 |

(*) Time on stream: 1 hour

Table 13 shows that the amounts of the catalyst filled to the individual catalyst layers are preferably equal.

EXAMPLE 13

1.0 g of the catalyst E was filled into each of the first-stage to fifth-stage catalyst layers of the same reaction apparatus as used in Example 2. At 500° C. under atmospheric pressure, a mixture of methanol and toluene in a mole ratio of 1:10 was fed into the first-stage catalyst layer at a WHSV of 775, and the same amount of methanol as that fed into the first-stage layer was fed into each of the second-stage to fifth-stage catalyst layers.

EXAMPLE 14

Example 13 was repeated except that the catalyst F was used instead of the catalyst E.

EXAMPLE 15

Example 14 was repeated except that the catalyst G was used instead of the catalyst F.

The results obtained in Example 13 to 15 are given in summarized in Table 14.

TABLE 14

| Example | 13 | 14 | 15 |
|---|---|---|---|
| Catalyst | E | F | G |
| Toluene conversion (%) | 18.8 | 21.4 | 21.5 |
| p-Xylene selectivity (%) | 85.4 | 78.7 | 84.1 |
| Methanol selectivity (%) | 36.3 | 40.9 | 41.4 |

TABLE 14-continued

| Example | 13 | 14 | 15 |
|---|---|---|---|
| Catalyst | E | F | G |
| Xylene yield (%) | 96.5 | 95.6 | 96.2 |

(*) Time on stream: 1 hour

The results given in Table 14 show that by using catalysts containing lanthanide oxide, the p-xylene selectivity can be increased to a level much higher than an ordinary thermodynamically equilibrium value.

EXAMPLE 16

1.0 g of the catalyst B was filled in each of the first-stage to fifth-stage catalyst layers in the same reaction apparatus as used in Example 2. At 500° C. under atmospheric pressure, a mixture of methanol and toluene in a mole ratio of 1:10 was fed into the first-stage catalyst layer at a WHSV of 68 together with hydrogen in an amount 10.5 molar times the amount of the toluene fed. The same amount of methanol as that fed into the first-stage layer was fed into each of the second-stage to fifth-stage catalyst layer. The results are shown in Table 15.

TABLE 15

| Time on stream (hours) | 2 | 11 | 29 |
|---|---|---|---|
| Toluene conversion (%) | 32.7 | 30.4 | 27.1 |
| p-Xylene selectivity (%) | 78.0 | 77.7 | 75.8 |
| Methanol selectivity (%) | 63.1 | 57.8 | 48.6 |
| Xylene yield (%) | 96.5 | 95.2 | 89.6 |

EXAMPLE 17

Example 16 was repeated except that the catalyst D was used instead of the catalyst B. The results are shown in Table 16.

TABLE 16

| Time of stream (hours) | 2 | 26 | 50 |
|---|---|---|---|
| Toluene conversion (%) | 34.5 | 30.1 | 18.3 |
| p-Xylene selectivity (%) | 73.2 | 72.6 | 69.5 |
| Methanol selectivity (%) | 66.9 | 57.1 | 24.3 |
| Xylene yield (%) | 97.0 | 94.8 | 93.1 |

Tables 15 and 16 show that the activities of the catalysts B and D are reduced rapidly.

EXAMPLE 18

1.0 g of the catalyst H was filled in each of the first-stage to fifth-stage catalyst layers of the same reaction apparatus as used in Example 2. At 400° C. under atmospheric pressure, the catalyst was reduced in an atmosphere of hydrogen for 2 hours. Thus, the catalyst contained 0.5% by weight of platinum and 5.0% by weight of magnesium and or its oxide based on the weight of the zeolite. At 500° C. under atmospheric pressure, a mixture of methanol and toluene in a mole ratio of 1:10 was fed into the first-stage catalyst layer at a WHSV of 68 together with hydrogen in an amount 10.5 molar times the amount of the toluene fed. The same amount of methanol as that fed into the first-stage catalyst layer was fed into each of the second-stage to fifth-stage catalyst layers. The results are shown in Table 17-1.

TABLE 17-1

| Time on stream (hours) | 2 | 26 | 50 | 106 |
|---|---|---|---|---|
| Toluene conversion (%) | 10.7 | 23.2 | 25.6 | 27.9 |
| p-Xylene selectivity (%) | 78.5 | 79.6 | 79.9 | 80.5 |
| Methanol selectivity (%) | 21.1 | 45.6 | 50.1 | 54.2 |
| Xylene yield (%) | 98.6 | 98.2 | 97.9 | 97.2 |

As shown in Table 17-1, the life of the magnesium oxide-modified catalyst can be prolonged by modifying it further with platinum.

Table 17-2 below shows the material balance when the time on stream is 106 hours.

TABLE 17-2

| Composition (wt. %) | Feed | Product |
|---|---|---|
| Gas | | |
| $CH_4$ | | 0.03 |
| $C_2H_6$ | | 0.24 |
| $C_2H_4$ | | 0.24 |
| $C_3H_8$ | | 0.05 |
| $C_4H_{10}$ | | 0.17 |
| CO | | 1.04 |
| $H_2$ | 16.26 | 16.41 |
| Liquid | | |
| non-aromatics | | 1.76 |
| benzene | | 0.01 |
| toluene | 71.34 | 51.44 |
| ethylbenzene | | 0.02 |
| p-xylene | | 17.93 |
| m-xylene | | 2.63 |
| o-xylene | | 1.72 |
| $Ca^+$ aromatics | | 0.68 |
| methanol | 12.40 | 0.0 |
| water | | 5.63 |

As shown in Table 17-2, per 100 parts by weight of toluene charged, the amount of toluene converted was 27.9 parts by weight and the amount of p-xylene formed was 25.1 parts by weight. In view of the fact that by an ordinary xylene isomerization method, 10 parts by weight of p-xylene is obtained per 100 parts by weight of the feed charge, and by a toluene transalkylation method, the amount of toluene converted is 45 parts by weight and the amount of p-xylene formed is 11 parts by weight per 100 parts of toluene charged, the efficiency of the apparatus in accordance with this invention is higher for synthesis of p-xylene and the process of the invention is industrially advantageous.

EXAMPLE 19

1.0 g of the catalyst I was filled in each of the first-stage to fifth-stage catalyst layers of the same reaction apparatus as used in Example 2. At 400° C. under atmospheric pressure, the catalyst was reduced in an atmosphere of hydrogen for 2 hours. As a result, the catalyst contained 0.5% by weight of platinum and 5.0% by weight of lanthanum and/or its oxide based on the zeolite. Using the modified catalyst, the same reaction as in Example 18 was carried out. The results are shown in Table 18.

TABLE 18

| Time on stream (hours) | 2 | 26 | 50 | 74 |
|---|---|---|---|---|
| Toluene conversion (%) | 25.4 | 29.5 | 29.6 | 28.4 |
| p-Xylene selectivity (%) | 72.5 | 71.5 | 72.3 | 72.9 |
| Methanol selectivity (%) | 50.0 | 56.8 | 56.4 | 53.8 |
| Xylene yield (%) | 98.4 | 96.2 | 95.3 | 94.8 |

It is seen from Table 18 that the life of the lanthanum oxide-modified catalyst can be prolonged by modifying it further with platinum.

EXAMPLE 20

1.0 g of the catalyst J was filled in each of the first-stage to fifth-stage catalyst layers of the same reaction apparatus as used in example 2. At 400° C. under atmospheric pressure, the catalyst was reduced in an atmosphere of hydrogen for 2 hours. As a result, the catalyst contained 0.5% by weight of rhodium and 5.0% by weight of magnesium and/or its oxide based on the zeolite. Using the modified catalyst, the same reaction as in Example 18 was carried out. The results are shown in Table 19.

TABLE 19

| Time on stream (hours) | 2 | 14 | 34 |
|---|---|---|---|
| Toluene conversion (%) | 29.5 | 29.9 | 25.6 |
| p-Xylene selectivity (%) | 71.6 | 75.4 | 77.3 |
| Methanol selectivity (%) | 55.4 | 57.2 | 49.4 |
| Xylene yield (%) | 93.9 | 95.6 | 96.4 |

It is seen from Table 19 that the life of the magnesium oxide-modified catalyst can be prolonged by modifying it further with rhodium.

EXAMPLE 21

1.0 g of the catalyst K was filled in each of the first-stage to fifth-stage catalyst layers of the same reaction apparatus as used in Example 2, and reduced in an atmosphere of hydrogen at 400° C. under atmospheric pressure for 2 hours. As a result, the modified catalyst contained 0.5% by weight of iridium and 5.0% by weight of magnesium and/or its oxide based on the zeolite. Using the modified catalyst, the same reaction as in Example 18 was carried out. The results are shown in Table 20.

TABLE 20

| Time on stream (hours) | 2 | 14 | 34 |
|---|---|---|---|
| Toluene conversion (%) | 21.1 | 31.5 | 30.1 |
| p-Xylene selectivity (%) | 77.3 | 79.4 | 80.4 |
| Methanol selectivity (%) | 60.3 | 61.0 | 57.9 |
| Xylene yield (%) | 96.9 | 96.8 | 96.2 |

It is seen from Table 20 that the life of the magnesium oxide-modified catalyst can be increased by modifying it further with iridium.

EXAMPLE 22

1.0 g of the catalyst L was filled in each of the first-stage to fifth-stage catalyst layers of the same reaction apparatus as used in Example 2, and reduced in an atmosphere of hydrogen at 400° C. and under atmospheric pressure for 2 hours. As a result, the modified catalyst contained 0.5% by weight of platinum, 0.25% by weight of iridium and 5.0% by weight of magnesium and/or its oxide based on the zeolite. Using the modified catalyst, the same reaction as in Example 18 was carried out. The results are shown in Table 21.

TABLE 21

| Time on stream (hours) | 2 | 14 | 34 |
|---|---|---|---|
| Toluene conversion (%) | 24.5 | 28.5 | 29.5 |
| p-Xylene selectivity (%) | 82.5 | 84.2 | 85.4 |
| Methanol selectivity (%) | 48.3 | 56.1 | 57.9 |
| Xylene yield (%) | 98.6 | 98.4 | 98.1 |

It is seen from Table 17-1 and 21 that the life of the catalyst modified with magnesium oxide can be further prolonged by modifying it further with platinum and iridium, and that the modified catalyst can give a higher toluene conversion in the initial stage of reaction than the catalyst H obtained by modifying the magnesium oxide-modified catalyst with platinum.

EXAMPLE 23

1.0 g of the catalyst M was filled in each of the first-stage to fifth-stage catalyst layers of the same reaction apparatus as used in Example 2, and reduced in an atmosphere of hydrogen at 400° C. under atmospheric pressure for 2 hours. As a result, the modified catalyst contained 0.5% by weight of platinum, 0.08% by weight of nickel and 5.0% by weight of magnesium and/or its oxide based on the zeolite. Using the modified catalyst, the same reaction as in Example 18 was carried out. The results are shown in Table 22.

TABLE 22

| Time on stream (hours) | 2 | 14 | 34 |
|---|---|---|---|
| Toluene conversion (%) | 21.2 | 25.8 | 26.9 |
| p-Xylene selectivity (%) | 78.4 | 80.3 | 82.0 |
| Methanol selectivity (%) | 41.8 | 50.7 | 52.8 |
| Xylene yield (%) | 98.7 | 98.4 | 98.2 |

Table 17-1 and 22 shows that the life of the catalyst modified with magnesium oxide can be prolonged by modifying it further with platinum and nickel, and that the catalyst can give a higher toluene conversion in the early stage of reaction than the catalyst H obtained by modifying the magnesium oxide-modified catalyst with platinum.

EXAMPLE 24

1.0 g of the catalyst B was filled in each of the first-stage to seventh-stage catalyst layers of the same reaction apparatus as used in Example 2. A mixture of methanol and toluene in a mole ratio of 1:10 was fed into the first-stage catalyst layer at a WHSV of 72.5. The same amount of methanol as that fed into the first-stage catalyst layer was fed into each of the second-stage to seventh-stage catalyst layers. The reaction was carried out under atmospheric pressure at 450° C. and 500° C., respectively. The results are shown in Table 23.

TABLE 23

| Reaction temperature (°C.) | 450 | 500 |
|---|---|---|
| Toluene conversion (%) | 20.0 | 25.5 |
| p-Xylene selectivity (%) | 73.9 | 73.0 |
| Methanol selectivity (%) | 26.2 | 33.4 |
| Xylene yield (%) | 91.5 | 91.8 |

(*) Time on stream: 1 hour

EXAMPLE 25

1.0 g of the catalyst H was filled in each of the first-stage to fifth-stage catalyst layers of the same reaction apparatus as used in Example 2, and reduced in an atmosphere of hydrogen under atmospheric pressure at 400° C. for 2 hours. As a result, the modified catalyst contained 0.5% by weight of platinum and 5.0% by weight of magnesium or its oxide based on the zeolite. A mixture of methanol and toluene in a mole ratio of 1:10 was fed into the first-stage catalyst layer at a WHSV of 68 together with hydrogen in an amount 10.5 molar times the amount of toluene fed by mol. The reaction was carried out at 500° C. and 2 kg/cm$^2$. G. The same amount of methanol as that fed into the first-stage catalyst layer was fed into each of the second-stage of fifth-stage catalyst layers. The results are shown in Table 24.

TABLE 24

| Time on stream (hours) | 2 | 26 | 50 |
|---|---|---|---|
| Toluene conversion (%) | 21.4 | 24.9 | 25.0 |
| p-Xylene selectivity (%) | 54.6 | 53.9 | 54.5 |
| Methanol selectivity (%) | 42.0 | 47.8 | 47.6 |
| Xylene yield (%) | 98.2 | 96.0 | 95.1 |

EXAMPLE 26

1.0 g of the catalyst H was filled in each of the first-stage and second-stage catalyst layers of the same reaction apparatus as used in Example 2, and reduced in an atmosphere of hydrogen at 400° C. under atmospheric pressure for 2 hours. As a result, the modified catalyst contained 0.5% by weight of platinum and 5.0% by weight of magnesium and/or its oxide based on the zeolite. Under atmospheric pressure at 500° C., toluene was fed into the first-stage catalyst layer at a WHSV of 34 together with dimethyl ether in a dimethyl ether/toluene ratio of 1:8 and hydrogen in a hydrogen/toluene ratio of 8.8, and the same amount of dimethyl ether as that fed into the first-stage layer was fed into the second-stage catalyst layer. The results are shown in Table 25.

TABLE 25

| Time on stream (hours) | 3 | 10 |
|---|---|---|
| Toluene conversion (%) | 30.3 | 28.2 |
| p-Xylene selectivity (%) | 85.8 | 84.0 |
| Dimethyl ether selectivity (%) | 54.8 | 50.4 |
| Xylene yield (%) | 90.4 | 89.4 |

The dimethyl ether selectivity as follows:

$$\text{Dimethyl ether selectivity (\%)} = \frac{\text{Moles of xylenes formed}}{\text{Moles of dimethyl ether fed}} \times \frac{100}{2}$$

Table 25 shows that dimethyl ether is effective as the methylating agent.

EXAMPLE 27

Using the catalysts A and B, the following Experiments A to D were conducted.

Experiment A 1.0 g of the catalyst A was filled in each of the first-stage and second-stage catalyst layers of the same reaction apparatus as used in Example 2. At 500° C. under atmospheric pressure, a mixture of methanol and toluene in a ratio of 1:4 was fed into the first-stage catalyst layer at a WHSV of 11.5, and the same amount of methanol as fed into the first-stage layer was fed into the second-stage layer.

Experiment B

Using the same reaction apparatus as used in Example 2, 1.0 g of the catalyst A was filled in the first-stage catalyst layer and 1.0 g of the catalyst B was filled in the second-stage catalyst layer. The same reaction as in Experiment A was carried out.

Experiment C

Using the same reaction apparatus as used in Example 2, 1.0 g of the catalyst B was filled in the first-stage layer and 1.0 g of the catalyst A was filled in the second-stage layer. The same reaction as in Experiment A was carried out.

Experiment D 1.0 g of the catalyst B was filled in the first-stage and second-stage catalyst layers of the same reaction apparatus as used in Example 2, and the same reaction as in Experiment A was carried out.

The results of these Experiments are shown in Table 26.

TABLE 27

| Experiment | A | B | C | D |
|---|---|---|---|---|
| Toluene conversion (%) | 15.2 | 19.0 | 19.0 | 22.2 |
| p-Xylene selectivity (%) | 83.0 | 63.7 | 71.8 | 57.6 |
| Methanol selectivity (%) | 27.5 | 33.6 | 33.4 | 40.1 |
| Xylene yield (%) | 90.4 | 88.5 | 87.8 | 90.4 |

(*) Time on stream: 1 hour

It is seen from Table 27 that by filling different catalysts in the catalyst layers, the performance of the methylation reaction can be changed.

EXAMPLE 28

The following Experiments A to C were carried out using the catalysts H, K and L.

Experiment A 1.0 g of the catalyst H was filled in each of the first-stage and second-stage catalyst layers of the same reaction apparatus as used in Example 2, and reduced in an atmosphere of hydrogen at 400° C. under atmospheric pressure for 2 hours. A mixture of methanol and toluene in a mole ratio of 1:4 was fed into the first-stage catalyst layer at a WHSV of 35 together with hydrogen in an amount 10.5 molar times the amount of the toluene fed and the same amount of methanol as that fed into the first-stage layer was fed into the second-stage layer.

Experiment B

Using the same reaction apparatus as used in Example 2, 1.0 g of the catalyst H was filled in the first-stage layer and 1.0 g of the catalyst K was filled in the second-stage layer. The catalysts were reduced in hydrogen under the same conditions as in Experiment A, and the same reaction as in Experiment A was carried out.

Experiment C

Using the same reaction apparatus as used in Example 2, 1.0 g of the catalyst H was filled in the first-stage layer and 1.0 g of the catalyst L was filled in the second-stage layer. The catalysts were reduced in hydrogen under the same conditions as in Experiment A, and the same reaction as in Experiment A was carried out.

The results of the Experiments are shown in Table 28. It is seen that the Experiments B and C showed a higher toluene conversion in the initial stage of reaction than Experiment A.

TABLE 28

| Experiment | | Time on stream (hours) | 2 | 14 | 34 |
|---|---|---|---|---|---|
| Experiment A | | Toluene conversion (%) | 9.1 | 13.8 | 20.1 |
| | | p-Xylene selectivity (%) | 78.5 | 79.0 | 79.7 |
| | | Methanol selectivity (%) | 17.6 | 26.6 | 28.6 |
| | | Xylene yield (%) | 96.6 | 96.2 | 95.9 |
| Experiment B | | Toluene conversion (%) | 17.4 | 19.9 | 22.7 |
| | | p-Xylene selectivity (%) | 76.1 | 78.2 | 79.7 |
| | | Methanol selectivity (%) | 33.8 | 38.5 | 43.7 |
| | | Xylene yield (%) | 97.0 | 96.8 | 96.3 |
| Experiment C | | Toluene conversion (%) | 14.7 | 18.7 | 24.3 |
| | | p-Xylene selectivity (%) | 80.1 | 81.4 | 82.1 |
| | | Methanol selectivity (%) | 28.8 | 36.5 | 47.3 |

What we claim is:

1. In a process for producing p-xylene which comprises catalytically methylating toluene with a methylating agent in the gaseous phase, the improvement wherein
    (a) said methylation is carried out continuously in a multi-stage reaction system consisting of a plurality of separate series-connected fixed catalyst layers without separating the resulting xylenes in an intermediate stage,
    (b) said toluene is fed together with hydrogen gas into only the first-stage fixed catalyst layer and passed successively through the subsequent fixed catalyst layers, the amount of toluene fed being such that the total weight hourly space velocity of toluene is from 1 to 300 hr$^{-1}$,
    (c) said methylating agent is fed into each of said fixed catalyst layers, if desired together with hydrogen gas, the amount of the methylating agent fed into each catalyst layer being $0.01/t$ moles to $1/t$ moles, in which t is the number of methyl groups in the methylating agent, per mole of toluene fed into the first-stage catalyst layer, and the total amount of the methylating agent fed into all of the catalyst layers being within the range of $0.1/t$ moles to $2/t$ moles, in which t is as defined, per mole of toluene fed into the first-stage catalyst layer, and
    (d) each fixed catalyst layer is filled with a catalyst composed of a crystalline aluminosilicate containing magnesium oxide or lanthanide oxide.

2. The process of claim 1 wherein the multi-stage reaction system contains 2 to 20 fixed catalyst layers.

3. The process of claim 1 wherein the total weight hourly space velocity of toluene is in the range of 2 to 200 hr$^{-1}$.

4. The process of claim 1 wherein the amount of hydrogen gas fed into the first-stage fixed catalyst layer is 0.5 to 20 moles per mole of toluene fed into the first-stage catalyst layer.

5. The process of claim 1 wherein the amount of the methylating agent to be fed into each of the catalyst layers is $0.02/t$ to $0.5/t$ moles, wherein t is as defined in claim 1, per mole of toluene fed into the first-stage catalyst layer.

6. The process of claim 1 wherein the amount (Qi) of the methylating agent fed into the ith stage catalyst layer satisfies the following inequality $$\frac{1}{t} \geq Qi \geq \frac{1}{i-1} \sum_{m=1}^{i-1} Qm$$

wherein Qi is the amount in moles of the methylating agent fed into the ith stage catalyst layer per mole of toluene fed into the first-stage catalyst layer, Qm is the amount in moles of the methylating agent fed into the mth stage catalyst layer per mole of the toluene fed into the first-stage catalyst layer, and t is as defined in claim 1.

7. The process of claim 1 wherein the total amount of the methylating agent fed into all of the catalyst layers is $0.1/t$ moles to $1.5/t$ moles per mole of toluene fed into the first-stage catalyst layer.

8. The process of claim 1 wherein the methylating agent is methanol or dimethyl ether or a mixture of these.

9. The process of claim 1 wherein the crystalline aluminosilicate has a silica/alumina mole ratio of at least 10.

10. The process of claim 1 wherein the catalyst contains 1 to 100% by weight of magnesium oxide based on the weight of the crystalline aluminosilicate.

11. The process of claim 1 wherein the catalyst contains 1 to 200% by weight of lanthanide oxide based on the weight of the aluminosilicate.

12. The process of claim 1 wherein the catalyst has an alpha value of 0.1 to 1,000.

13. The process of claim 1 wherein the catalyst has a weight ratio of cyclohexane to n-hexane sorptive capacity at 25° C. of 0.05 to 0.7.

14. The process of claim 1 wherein the catalyst further contains platinum, rhodium and or iridium.

15. The process of claim 15 wherein the catalyst contains 0.1 to 5% by weight of platinum, rhodium and/or iridium based on the weight of the aluminosilicate.

16. The process of claim 1 wherein the crystalline aluminosilicate is zeolite ZSM-5.

17. The process of claim 1 wherein the amount (Wi) of the catalyst filled in the ith stage fixed catalyst layer satisfies the following inequality $$\frac{0.5}{n} \sum_{m=1}^{n} Wm < Wi < \frac{1.5}{n} \sum_{m=1}^{n} Wm$$

wherein Wi is the weight of the catalyst filled in the ith stage catalyst layer, Wm is the amount of the catalyst filled in the mth stage fixed catalyst layer, and n is the total number of the fixed catalyst layers used.

18. The process of claim 1 wherein the temperature of the inside of each catalyst layer is maintained at 250° to 700° C.

19. The process of claim 1 wherein the pressure of the inside of each catalyst layer is maintained at 1 to 20 atmospheres.

* * * * *

UNITED STATES PATENT AND TRADEMARK OFFICE
CERTIFICATE OF CORRECTION

PATENT NO. : 4,377,718
DATED : March 22, 1983
INVENTOR(S) : Kimihiko Sato; Tokuju Sakai; Yasuo Yamasaki; Tamio Onodera; Koji Sumitani.

It is certified that error appears in the above—identified patent and that said Letters Patent is hereby corrected as shown below:

Claim 15, line 36, should refer to claim "14"

Signed and Sealed this

Twenty-fourth Day of May 1983

[SEAL]

Attest:

DONALD J. QUIGG

Attesting Officer     Acting Commissioner of Patents and Trademarks